United States Patent
Duffy et al.

(10) Patent No.: US 7,241,783 B2
(45) Date of Patent: Jul. 10, 2007

(54) THROMBOPOIETIN MIMETICS

(75) Inventors: Kevin J. Duffy, Collegeville, PA (US); Juan I. Luengo, Collegeville, PA (US); Stephen G. Miller, San Diego, CA (US); Julian Jenkins, Collegeville, PA (US); Alan T. Price, Collegeville, PA (US); Antony N. Shaw, Collegeville, PA (US)

(73) Assignees: SmithKline Beecham Corporation, Philadelphia, PA (US); Ligand Pharmaceutical, San Diego, CA (US)

( * ) Notice: Subject to any disclaimer, the term of this patent is extended or adjusted under 35 U.S.C. 154(b) by 344 days.

(21) Appl. No.: 10/451,300

(22) PCT Filed: Dec. 19, 2001

(86) PCT No.: PCT/US01/50774

§ 371 (c)(1),
(2), (4) Date: Jun. 19, 2003

(87) PCT Pub. No.: WO02/49413

PCT Pub. Date: Jun. 27, 2002

(65) Prior Publication Data

US 2004/0058990 A1 Mar. 25, 2004

Related U.S. Application Data

(60) Provisional application No. 60/256,622, filed on Dec. 19, 2000.

(51) Int. Cl.
*A61K 31/427* (2006.01)
*A61K 31/4709* (2006.01)
*A61K 31/4152* (2006.01)

(52) U.S. Cl. .................. 514/369; 514/310; 514/404
(58) Field of Classification Search ................ 514/369, 514/404, 150, 479, 528, 581, 590
See application file for complete search history.

(56) References Cited

U.S. PATENT DOCUMENTS 5,376,451 A * 12/1994 Albin et al. ............. 428/402.2
6,552,008 B1 * 4/2003 Duffy et al. ................ 514/150
6,720,345 B1 * 4/2004 Luengo et al. ............. 514/369

FOREIGN PATENT DOCUMENTS

| DE | 286580 A | * | 1/1991 |
| DE | 290184 A | * | 5/1991 |
| EP | 433526 A1 | * | 6/1991 |
| WO | WO 99/11262 | | 3/1999 |
| WO | WO 00/28987 | | 5/2000 |
| WO | WO 01/34585 | | 5/2001 |

OTHER PUBLICATIONS ("Arylhydrozones and Phenylsemicarbazones of 2-aminobenzophenones as Antithrombotic agents", Andronati et al., Pharmazie, abstract, 1995, 50(9), 632-3.*
"Synthesis and Biological Evaluation of a New Series of Potential Beta Blockers with Dual Pharmacological Actions", Viswanathan et al., Indian Drugs, abstact, 1990, 27(1), 513-15.*

* cited by examiner

*Primary Examiner*—Brian Kwon
(74) *Attorney, Agent, or Firm*—Wayne J. Dustman; Steve Venetianer; Charles M Kinzig

(57) ABSTRACT

Invented are non-peptide TPO mimetics. Also invented is a method of treating thrombocytopenia, in a mammal, including a human, in need thereof which comprises administering to such mammal an effective amount of a selected substituted thiosemicarbazone derivative.

1 Claim, No Drawings

THROMBOPOIETIN MIMETICS

CROSS REFERENCES TO RELATED APPLICATIONS

This application is a National Stage Application filed under 35 U.S.C.0371 of PCT/US01/50774, filed on Dec. 19, 2001, which claims priority of U.S. Provisional Application No. 60/256,622, filed Dec. 19, 2000.

FIELD OF THE INVENTION

This invention relates to thrombopoietin (TPO) mimetics and their use as promoters of thrombopoiesis and megakaryocytopoiesis.

BACKGROUND OF THE INVENTION

Thrombopoietin (TPO) is a 332-amino acid glycosylated polypeptide which plays a key role in the regulation of megakaryocytopoiesis, the process in which platelets are produced from bone marrow megakaryocytes. See Kuter et al.,*Proc. Natl. Acad. Sci. USA* 91: 11104–11108 (1994); Barley et al., *Cell* 77:1117–1124 (1994); Kaushansky et al., *Nature* 369:568–571 (1994); Wendling et al., *Nature* 369: 571–574 (1994); and Sauvage et al., *Nature* 369: 533–538 (1994). IPO is produced in the liver but exerts its main function in the bone marrow, where it stimulates the differentiation of stem cells into megakaryocyte progenitors as well as megakaryocyte proliferation, polyploidization and, ultimately, their fragmentation into circulating platelet bodies. TPO is also the primary regulator of situations involving thrombocytopenia and has been shown in a number of studies to increase platelet counts, increase platelet size, and increase isotope incorporation into platelets of recipient animals. See, e.g., Metcalf Nature 369:519–520 (1994). Specifically, TPO is thought to affect megakaryocytopoiesis in several ways: (1) it produces increases in megakaryocyte size and number; (2) it produces an increase in DNA content, in the form of polyploidy, in megakaryocytes; (3) it increases megakaryocyte endomitosis; (4) it produces increased maturation of megakaryocytes; and (5) it produces an increase in the percentage of precursor cells, in the form of small acetylcholinesterase-positive cells, in the bone marrow.

Platelets are necessary for blood clotting and when their numbers are very low a patient is at risk of death from catastrophic hemorrhage. Thus, TPO has potential useful application in both the diagnosis and the treatment of various hematological disorders, for example, diseases primarily due to platelet defects. Likewise, TPO has potential application in the treatment of thrombocytopenic conditions, especially those derived from chemotherapy, radiation therapy, or bone marrow transplantation as treatment for cancer or lymphoma. Indeed, ongoing clinical trials in cancer patients have shown that recombinant human TPO is effective in decreasing the platelet nadir and enhancing platelet recovery when given with high-dose carboplatin chemotherapy. See Basser Blood, 1997, 89: 3118. Similar results have also been obtained in clinical studies with pegylated megakaryocyte differentiation factor (peg-MGDF, a pegylated truncated N-terminal fragment of human TPO). See e.g., Fanucchi (1997) N Engl J Med, 336: 404.

Because the slow recovery of platelet levels in patients suffering from thrombocytopenia is a serious problem, it would be desirable to provide compounds which allow for the treatment of thrombocytopenia by acting as a TPO mimetic. A few years ago, the development of TPO peptide mimetics was reported (WO 96/4018, WO 96/40750, WO 98/25965). These peptides were designed to bind and activate the TPO-R but have no sequence homology to the natural TPO. In recent years, a number of small-molecule agents with TPO mimetic activity been reported. These include 1,4-benzodiazepin-2-ones (JP11001477), metal complexes derived from Schiff base ligands (WO 99/11262), cyclic polyamine derivatives (WO 00/28987), thiazol-2-yl-benzamides (WO 01/07423, WO 01/53267), azo-aryl derivatives (WO 00/35446, WO 1/17349), 2-aryl-naphthimidazoles (WO 01/39773, WO 01/53267) and semicarbazone derivatives (WO 01/34585). In cell-based systems, all these molecules can activate signal transduction pathways that are dependent on the presence of the TPO receptor on the cell membrane, suggesting some type of direct interaction with the TPO receptor itself. As disclosed herein it has unexpectedly been discovered that certain substituted thiosemicarbazone derivatives are very effective and potent agonists of the TPO receptor. Some of the most preferred compounds of this class were found to stimulate the proliferation and differentiation of TPO-responsive human cell lines and human bone marrow cultures with full TPO efficacy at concentrations below 100 nM.

SUMMARY OF THE INVENTION

This invention relates to compounds of Formula (I):

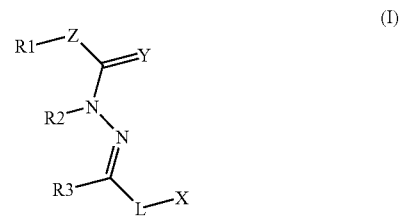

wherein:
R¹ is aryl, optionally substituted with 1 or more substituents selected from $C_{1-10}$alkyl, aryl, heteroaryl, halogen, —C(O)OR⁷, —CONR⁷R⁸, —S(O)$_n$R⁶, —S(O)$_2$NR⁷R⁸, sulfonyloxy, nitro, optionally substituted amino, hydroxy, alkoxy;

R² is selected from hydrogen, $C_{1-12}$alkyl, aryl, substituted aryl, and alkyl substituted with one or more substituents selected from the group consisting of: alkoxy, acyloxy, aryl, substituted aryl, amino, N-acylamino, oxo, hydroxy, cycloalkyl, substituted cycloalkyl, —C(O)OR⁷, —S(O)$_2$NR⁷R⁸, —S(O)$_n$R⁶, aryloxy, nitro, cyano, halogen, and protected —OH, where
R⁶ is selected from hydrogen, alkyl, cycloalkyl, $C_1$–$C_{12}$aryl, substituted alkyl, substituted cycloalkyl and substituted $C_1$–$C_{12}$aryl, and R⁷ and R⁸ are independently selected from hydrogen, cycloalkyl, aryl, substituted cycloalkyl, substituted aryl, alkyl or alkyl substituted with one or more substituents selected from the group consisting of: alkoxy, acyloxy, aryloxy, amino, N-acylamino, oxo, hydroxy, —C(O)OR⁶, —S(O)$_n$R⁶, C(O)NR⁶R⁶, —SO$_2$NR⁶R⁶, nitro, cyano, cycloalkyl, substituted cycloalkyl, halogen, $C_1$–$C_{12}$aryl, substituted $C_1$–$C_{12}$aryl and protected —OH where R⁶ is as described above;

n is 0–3;

Z is selected from S or NR², where R² is as defined above;

R³ is selected from hydrogen, $C_1$–$C_{10}$alkyl, phenyl, substituted phenyl, carboxyl or —$C_1$–$C_{10}$alkoxycarbonyl;

L is naphthyl or a group of formula (L):

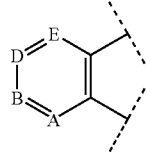

(L)

where A, B, D and E independently represent $CR^{11}$ or N; where $R^{11}$ is selected from hydrogen, halogen, —$CF_3$, —CN, —$SO_3H$, —$SO_3Na$, —$SO_2R^{14}$, —$NO_2$, phenyl, substituted phenyl, $C_1$–$C_{10}$alkyl, $C_1$–$C_{10}$alkoxy, $C_1$–$C_{10}$acyloxy, arylalkoxy, —$COR^{14}$, —$NR^{12}R^{13}$, hydroxy or cycloalkyl;

where $R^{14}$ is selected from hydroxy, $C_1$–$C_{10}$alkyl, phenyl, amino, mono- or dialkylamino;

$R^{12}$ and $R^{13}$ are independently selected from hydrogen, $C_1$–$C_{10}$allyl, $C_1$–$C_{12}$aryl, substituted $C_1$–$C_{12}$aryl, $C_1$–$C_{10}$acyl or cycloalkyl;

or either A=B or D=E alternatively represent O, S or $NR^{12}$; where $R^{12}$ is as defined above;

Y is selected from —S, —O and —$NR^{15}$, where $R^{15}$ is selected from hydrogen, $C_1$–$C_{10}$alkyl, substituted $C_1$–$C_{10}$alkyl, $C_1$–$C_6$alkylphenyl, substituted $C_1$–$C_6$alkylphenyl, $C_1$–$C_{10}$acyl, substituted $C_1$–$C_{10}$acyl, or $SO_2R^9$, where $R^9$ is $C_1$–$C_{10}$alkyl, substituted $C_1$–$C_{10}$alkyl, $C_1$–$C_{12}$aryl or substituted $C_1$–$C_{12}$aryl; and X is selected from —$SR^{16}$, —$OR^{16}$ or —$NHR^{17}$; where $R^{16}$ is hydrogen, $C_1$–$C_{10}$alkyl or substituted $C_1$–$C_{10}$alkyl;

$R^{17}$ is hydrogen, $C_1$–$C_{10}$alkyl, substituted $C_1$–$C_{10}$alkyl, $C_1$–$C_6$alkylphenyl, $C_1$–$C_{10}$acyl or substituted $C_1$–$C_{10}$acyl; and pharmaceutically acceptable salts, hydrates, solvates and esters thereof.

This invention relates to a method of treating thrombocytopenia, which comprises administering to a subject in need thereof an effective amount of a TPO mimetic compound of Formula (I).

The present invention also relates to the discovery that the compounds of Formula (I) are active as agonists of the TPO receptor.

In a further aspect of the invention there is provided novel processes and novel intermediates useful in preparing the presently invented TPO mimetic compounds.

Included in the present invention are pharmaceutical compositions comprising a pharmaceutical carrier and compounds useful in the methods of the invention.

Also included in the present invention are methods of co-administering the presently invented TPO mimetic compounds with further active ingredients.

DETAILED DESCRIPTION OF THE INVENTION

This invention relates to compounds of Formula (I) as described above.

Preferred among the presently invented Formula I compounds are those in which $R^1$ is $C_1$–$C_{12}$aryl, particularly phenyl, substituted with a carboxy or sulfonic acid substituent.

Preferred among the presently invented Formula I compounds are those in which $R^1$ and $R^2$ are independently selected from hydrogen, $C_{1-10}$alkyl, $C_{1-12}$aryl and substituted $C_{1-12}$aryl.

Preferred among the presently invented Formula I compounds are those in which:

Z is S or $NR^2$ where $R^2$ is as defined above;

L is $C_3$–$C_6$aryl optionally substituted with form 1 to 3 substituents selected from the group consisting of: hydroxy, nitro, —C(O)OH, alkyl, substituted alkyl, $C_{1-12}$aryl, substituted $C_{1-12}$aryl, Br, $C_1$, $CF_3$ and F;

Y is S; and

X is —OH or methoxy; and pharmaceutically acceptable salts, hydrates, solvates and esters thereof.

Also preferred among the presently invented Formula I compounds are those in which:

$R^1$ is phenyl, substituted with either carboxylic acid or sulfonic acid;

Z, $R^2$, $R^3$, L, X and Y are as described in claim 1; and pharmaceutically acceptable salts, hydrates, solvates and esters thereof.

Also preferred among the presently invented Formula I compounds are those in which:

Z is NH;

$R^2$ and $R^3$ are hydrogen;

Y=S;

$R^1$, L, X are as described in claim 1; and pharmaceutically acceptable salts, hydrates, solvates and esters thereof.

Also preferred among the presently invented Formula I compounds are those in which:

L is selected from 3-biphenyl, 4-biphenyl or 1-N-phenylpyrazole substituted with from 1 to 3 substituents selected from the group consisting of: nitro, alkyl, substituted alkyl, Br, Cl, $CF_3$ and F;

X=OH;

Z, $R^1$, $R^2$, $R^3$ and Y are as described in claim 1; and pharmaceutically acceptable salts, hydrates, solvates and esters thereof.

Also preferred among the presently invented Formula I compounds are compounds of formula (II) wherein:

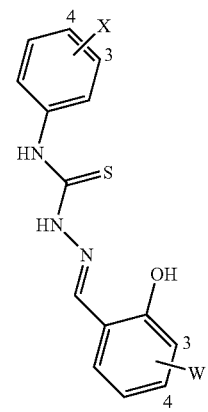

(II)

X is selected from 3-carboxylic acid, 4-carboxylic acid, 3-sulfonic acid or 4-sulfonic acid;

W is selected from 3-phenyl or 4-phenyl; in either case substituted with from 1 to 3 substituents selected from the group consisting of: nitro, alkyl, substituted alkyl, Br, Cl, CF$_3$ and F; and pharmaceutically acceptable salts, hydrates, solvates and esters thereof.

Also preferred among the presently invented Formula I compounds are compounds of formula (H) wherein:

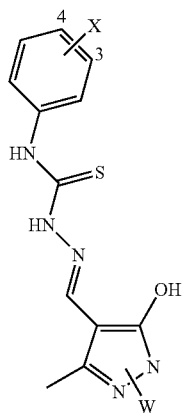

(III)

X is selected from 3-carboxylic acid, 4-carboxylic acid, 3-sulfonic acid or 4-sulfonic acid;

W is N-phenyl substituted with from 1 to 3 substituents selected from the group consisting of: nitro, alkyl, substituted alkyl, Br, Cl, CF$_3$ and F; and pharmaceutically acceptable salts, hydrates, solvates and esters thereof.

Most preferred among the presently invented Formula I compounds are those in which:

$R^1$ is phenyl substituted with either a carboxy or sulfonic acid;

Z is NH;

$R^2$ and $R^3$ are hydrogen;

L is either 3-biphenyl, 4-biphenyl or 1-N-phenylpyrazole substituted with from 1 to 3 substituents selected from the group consisting of: nitro, alkyl, substituted alkyl, Br, Cl, CF$_3$ and F;

X=OH; and pharmaceutically acceptable salts, hydrates, solvates and esters thereof.

Preferred among the presently invented compounds are:

4-(naphth-1-yl)-1-(2,4,6-trihydroxybenzylidene)-3-thiosemicarbazide;

1-(3,5-dichloro-2-hydroxybenzylidene)4-(4-sulfophenyl)-3-thiosemicarbazide;

1-[(2-hydroxynaphth-1-yl)methylidene]-4-(4-sulfophenyl)-3-thiosemicarbazide;

4-(4-carboxyphenyl)-1-(3,5-dichloro-2-hydroxybenzylidene)-3-thiosemicarbazide;

1-[1-(4-carboxy-2-hydroxyphenyl)ethylidene]-4-(naphth-1-yl)-3-thiosemicarbazide;

4-(4-carboxyphenyl)-1-[(2-hydroxynaphth-1-yl)methylidene]-3-thiosemicarbazide;

4-(3-carboxyphenyl)-1-[(2-hydroxynaphth-1-yl)methylidene]-3-thiosemicarbazide;

4-(3-carboxyphenyl)-1-(3,5-dichloro-2-hydroxybenzylidene)-3-thiosemicarbazide;

1-(4-carboxy-2-hydroxybenzylidene)-4-(naphth-1-yl)-3-thiosemicarbazide;

4-(4-carboxyphenyl)-1-(3,5-dibromo-2-hydroxybenzylidene)-3-thiosemicarbazide;

4-(3-carboxyphenyl)-1-(3,5-dibromo-2-hydroxybenzylidene)-3-thiosemicarbazide;

1-(4-benzyloxy-2-hydroxybenzylidene)-4-(4-carboxyphenyl)-3-thiosemicarbazide;

1-(4-benzyloxy-2-hydroxybenzylidene)-4-(3-carboxyphenyl)-3-thiosemicarbazide;

4-(3-carboxyphenyl)-1-(5-chloro-2-hydroxybenzylidene)-3-thiosemicarbazide;

4-(4-carboxyphenyl)-1-[(1-hydroxynaphth-2-yl)methylidene]-3-thiosemicarbazide;

4-(3-carboxyphenyl)-1-[(1-hydroxynaphth-2-yl)methylidene]-3-thiosemicarbazide;

4-(4-carboxyphenyl)-1-(3,5-di-t-butyl-2-hydroxybenzylidene)-3-thiosemicarbazide;

4-(3-carboxyphenyl)-1-(3,5-di-t-butyl-2-hydroxybenzylidene)-3-thiosemicarbazide;

4-(4-carboxyphenyl)-1-(2-hydroxy-3-methylbenzylidene)-3-thiosemicarbazide;

4-(3-carboxyphenyl)-1-(2-hydroxy-3-methylbenzylidene)-3-thiosemicarbazide;

4-(3-carboxyphenyl)-1-(2-hydroxy-5-methylbenzylidene)-3-thiosemicarbazide;

1-(2,4-dihydroxybenzylidene)-4-(naphth-1-yl)-3-thiosemicarbazide;

1-(2-hydroxy-3-carboxybenzylidene)-4-(2-phenylphenyl)-3-thiosemicarbazide;

4-(3-chloro-2-methylphenyl)-1-(2-hydroxy-4-carboxybenzylidene)-3-thiosemicarbazide;

1-(2-hydroxy-4-carboxybenzylidene)-4-(2-phenylphenyl)-3-thiosemicarbazide;

4-(3-chloro-4-methylphenyl)-1-(2-hydroxy-4-carboxybenzylidene)-3-thiosemicarbazide;

1-(2-hydroxy-4-carboxybenzylidene)-4-(4-methylphenyl)-3-thiosemicarbazide;

4-(4-carboxyphenyl)-1-[2-methoxy-3-(4-methylphenyl)benzylidene]-3-thiosemicarbazide;

4-(3-carboxyphenyl)-1-[3-(4-fluorophenyl)-2-methoxybenzylidene]-3-thiosemicarbazide;

4-(4-carboxyphenyl)-1-[3-(4-chlorophenyl)-2-methoxybenzylidene]-3-thiosemicarbazide;

4-(3-carboxyphenyl)-1-[3-(4-chlorophenyl)-2-methoxybenzylidene]-3-thiosemicarbazide;

4-(4-carboxyphenyl)-1-[3-(dibenzo[b,d]furan-1-yl)-2-methoxybenzylidene]-3-thiosemicarbazide;

4-(4-carboxyphenyl)-1-[2-hydroxy-3-(2-methylphenyl)benzylidene]-3-thiosemicarbazide;

4-(3-carboxyphenyl)-1-[2-hydroxy-3-(2-methylphenyl)benzyfidene]-3-thiosemicarbazide;

4-(4-carboxyphenyl)-1-[3-(3,4-dimethylphenyl)-2-hydroxybenzylidene]-3-thiosemicarbazide;

4-(3-carboxyphenyl)-1-[3-(3,4-dimethylphenyl)-2-hydroxybenzylidene]-3-thiosemicarbazide;

4-(4-carboxyphenyl)-1-[2-hydroxy-3-(3-trifluoromethylphenyl)benzylidene]-3-thiosemicarbazide;

4-(3-carboxyphenyl)-1-[2-hydroxy-3-(3-trifluoromethylphenyl)benzylidene]-3-thiosemicarbazide;

4-(4-carboxyphenyl)-1-[3-(4-fluorophenyl)-2-hydroxybenzyhidene]-3-thiosemicarbazide;

4-(3-carboxyphenyl)-1-[3-(4-chlorophenyl)-2-bydroxybenzylidene]-3-thiosemicarbazide;

4-(4-carboxyphenyl)-1-[3-(dibenzo[b,d]furan-1-yl)-2-hydroxybenzylidene]-3-thiosemicarbazide;
4-(3-carboxyphenyl)-1-[3-(dibenzo[b,d]furan-1-yl)-2-hydroxybenzylidene]-3-thiosemicarbazide;
4-(4-carboxyphenyl)-1-[2-hydroxy-3-(naphth-1-yl)benzylidene]-3-thiosemicarbazide;
4-(3-carboxyphenyl)-1-[2-hydroxy-3-(naphth-1-yl)benzylidene]-3-thiosemicarbazide;
4-(4-carboxyphenyl)-1-[3-(3-chlorophenyl)-2-hydroxybenzylidene]-3-thiosemicarbazide;
4-(3-carboxyphenyl)-1-[3-(3-chlorophenyl)-2-hydroxybenzylidene]-3-thiosemicarbazide;
4-(4-carboxyphenyl)-1-[2-hydroxy-3-(3-nitrophenyl)benzylidene]-3-thiosemicarbazide;
4-(3-carboxyphenyl)-1-[2-hydroxy-3-(3-nitrophenyl)benzylidene]-3-thiosemicarbazide;
4-(4-carboxyphenyl)-1-(2-hydroxy-4-phenylbenzylidene)-3-thiosemicarbazide;
4-(3-carboxyphenyl)-1-(2-hydroxy-4-phenylbenzylidene)-3-thiosemicarbazide;
4-(4-carboxyphenyl)-1-[{11-(4-chlorophenyl)-5-hydroxy-3-methylpyrazol-4-yl}methylene]-3-thiosemicarbazide;
4-(3-carboxyphenyl)-1-[{1-(4-chlorophenyl)-5-hydroxy-3-methylpyrazol-4-yl}methylene]-3-thiosemicarbazide;
4-(4-carboxyphenyl)-1-[(5-hydroxy-3-methyl-1-phenylpyrazol-4-yl)methylene]-3-thiosemicarbazide;
4-(3-carboxyphenyl)-1-[(5-hydroxy-3-methyl-1-phenylpyrazol-4-yl)methylene]-3-thiosemicarbazide;
4-(4-carboxyphenyl)-1-[{(1-(3,4-dimethylphenyl)-5-hydroxy-3-methylpyrazol-4-yl }methylene]-3-thiosemicarbazide;
4-(3-carboxyphenyl)-1-[{1-(3,4-dimethylphenyl)-5-hydroxy-3-methylpyrazol-4-yl}methylene]-3-thiosemicarbazide;
4-(4-carboxyphenyl)-1-[{d-hydroxy-3-methyl-1-(4-methylphenyl)pyrazol-4-yl}-methylenel]-3-thiosemicarbazide;
4-(3-carboxyphenyl)-1-[{5-hydroxy-3-methyl-1-(4-methylphenyl)pyrazol-4-yl}methylene]-3-thiosemicarbazide;
4-(4-carboxyphenyl)-1-[{1-(3-chlorophenyl)-5-hydroxy-3-methylpyrazol-4-yl}methylene]-3-thiosemicarbazide; and
4-(3-carboxyphenyl)-1-[{1-(3-chlorophenyl)-5-hydroxy-3-methylpyrazol-4-yl}methylene]-3-thiosemicarbazide.

Preferred compounds for use in the presently invented compositions and methods are:
4-(4-chloro-2-methylphenyl)-1-(3,5-dinitro-2-hydroxybenzylidene)-3-thiosemicarbazide;
1-(3,5-dinitro-2-hydroxybenzylidene)-4-(2-methylphenyl)-3-thiosemicarbazide;
1-(3,5-dichloro-2-hydroxybenzylidene)-4(4-ethoxycarbonylphenyl)-3-thiosemicarbazide;
4-(naphth-1-yl)-1-(2,4,6-trihydroxybenzylidene)-3-thiosemicarbazide;
1-(3,5-dichloro-2-hydroxybenzylidene)-4(4-sulfophenyl)-3-thiosemicarbazide;
1-[(2-hydroxynaphth-1-yl)methylidene]4(4-sulfophenyl)-3-thiosemicarbazide;
4-(4-carboxyphenyl)-1-(3,5-dichloro-2-hydroxybenzylidene)-3-thiosemicarbazide;
1-[1-(4-carboxy-2-hydroxyphenyl)ethylidene]4-(naphth-1-yl)-3-thiosemicarbazide;
4-(4-carboxyphenyl)-1-[(2-hydroxynaphth-1-yl)methylidene]-3-thiosemicarbazide;
4-(3-carboxyphenyl)-1-[(2-hydroxynaphth-1-yl)methylidene]-3-thiosemicarbazide;
4-(3-carboxyphenyl)-1-(3,5-dichloro-2-hydroxybenzylidene)-3-thiosemicarbazide;
1-(4-carboxy-2-hydroxybenzylidene)-4-(naphth-1-yl)-3-thiosemicarbazide;
4-(4-carboxyphenyl)-1-(3,5-dibromo-2-hydroxybenzylidene)-3-thiosemicarbazide;
4-(3-carboxyphenyl)-1-(3,5-dibromo-2-hydroxybenzylidene)-3-thiosemicarbazide;
1-(4-benzyloxy-2-hydroxybenzylidene)-4-(4-carboxyphenyl)-3-thiosemicarbazide;
1-(4-benzyloxy-2-hydroxybenzylidene)-4-(3-carboxyphenyl)-3-thiosemicarbazide;
4-(3-carboxyphenyl)-1-(5-chloro-2-hydroxybenzylidene)-3-thiosemicarbazide;
4-(4-carboxyphenyl)-1-[(1-hydroxynaphth-2-yl)methylidene]-3-thiosemicarbazide;
4-(3-carboxyphenyl)-1-[(1-hydroxynaphth-2-yl)methylidene]-3-thiosemicarbazide;
4-(4-carboxyphenyl)-1-(3,5-di-t-butyl-2-hydroxybenzylidene)-3-thiosemicarbazide;
4-(3-carboxyphenyl)-1-(3,5-di-t-butyl-2-hydroxybenzylidene)-3-thiosemicarbazide;
4-(4-carboxyphenyl)-1-(2-hydroxy-3-methylbenzylidene)-3-thiosemicarbazide;
4-(3-carboxyphenyl)-1-(2-hydroxy-3-methylbenzylidene)-3-thiosemicarbazide;
4-(3-carboxyphenyl)-1-(2-hydroxy-5-methylbenzylidene)-3-thiosemicarbazide;
1-(2,4-dihydroxybenzylidene)-4-(naphth-1-yl)-3-thiosemicarbazide;
1-(2-hydroxy-3-carboxybenzylidene)-4-(2-phenylphenyl)-3-thiosemicarbazide;
4-(3-chloro-2-methylphenyl)-1-(2-hydroxy-4-carboxybenzylidene)-3-thiosemicarbazide;
1-(2-hydroxy-4-carboxybenzylidene)-4-(2-phenylphenyl)-3-thiosemicarbazide;
4-(3-chloro-4-methylphenyl)-1-(2-hydroxy-4-carboxybenzylidene)-3-thiosemicarbazide;
1-(2-hydroxy-4-carboxybenzylidene)-4-(4-methylphenyl)-3-thiosemicarbazide;
4-(4-carboxyphenyl)-1-[2-methoxy-3-(4-methylphenyl)benzylidene]-3-thiosemicarbazide;
4-(3-carboxyphenyl)-1-[3-(4-fluorophenyl)-2-methoxybenzylidene]-3-thiosemicarbazide;
4-(4-carboxyphenyl)-1-[3-(4-chlorophenyl)-2-methoxybenzylidene]-3-thiosemicarbazide;
4-(3-carboxyphenyl)-1-[3-(4-chlorophenyl)-2-methoxybenzylidene]-3-thiosemicarbazide;
4-(4-carboxyphenyl)-1-[3-(dibenzo[b,d]furan-1-yl)-2-methoxybenzylidene]-3-thiosemicarbazide;
4-(4-carboxyphenyl)-1-[2-hydroxy-3-(2-methylphenyl)benzylidene]-3-thiosemicarbazide;
4-(3-carboxyphenyl)-1-[2-hydroxy-3-(2-methylphenyl)benzylidene]-3-thiosemicarbazide;
4-(4-carboxyphenyl)-1-[3-(3,4-dimethylphenyl)-2-hydroxybenzylidene]-3-thiosemicarbazide;
4-(3-carboxyphenyl)-1-[3-(3,4-dimethylphenyl)-2-hydroxybenzylidene]-3-thiosemicarbazide;
4-(4-carboxyphenyl)-1-[2-hydroxy-3-(3-trifluoromethylphenyl)benzylidene]-3-thiosemicarbazide;
4-(3-carboxyphenyl)-1-[2-hydroxy-3-(3-trifluoromethylphenyl)benzylidene]-3-thiosemicarbazide;
4-(4-carboxyphenyl)-1-[3-(4-fluorophenyl)-2-hydroxybenzylidene]-3-thiosemicarbazide;
4-(3-carboxyphenyl)-1-[3-(4-chlorophenyl)-2-hydroxybenzylidene]-3-thiosemicarbazide;

4-(4-carboxyphenyl)-1-[3-(dibenzo[b,d]furan-1-yl)-2-hydroxybenzylidene]-3-thiosemicarbazide;
4-(3-carboxyphenyl)-1-[3-(dibenzo[b,d]furan-1-yl)-2-hydroxybenzylidene]-3-thiosemicarbazide;
4-(4-carboxyphenyl)-1-[2-hydroxy-3-(naphth-1-yl)benzylidene]-3-thiosemicarbazide;
4-(3-carboxyphenyl)-1-[2-hydroxy-3-(naphth-1-yl)benzylidene]-3-thiosemicarbazide;
4-(4-carboxyphenyl)-1-[3-(3-chlorophenyl)-2-hydroxybenzylidene]-3-thiosemicarbazide;
4-(3-carboxyphenyl)-1-[3-(3-chlorophenyl)-2-hydroxybenzylidene]-3-thiosemicarbazide;
4-(4-carboxyphenyl)-1-[2-hydroxy-3-(3-nitrophenyl)benzylidene]-3-thiosemicarbazide;
4-(3-carboxyphenyl)-1-[2-hydroxy-3-(3-nitrophenyl)benzylidene]-3-thiosemicarbazide;
4-(4-carboxyphenyl)-1-(2-hydroxy-4-phenylbenzylidene)-3-thiosemicarbazide;
4-(3-carboxyphenyl)-1-(2-hydroxy-4-phenylbenzylidene)-3-thiosemicarbazide;
4-(4-carboxyphenyl)-1-[{1-(4-chlorophenyl)-5-hydroxy-3-methylpyrazol-4-yl}methylene]-3-thiosemicarbazide;
4-(3-carboxyphenyl)-1-[{1-(4-chlorophenyl)-5-hydroxy-3-methylpyrazol-4-yl}methylene]-3-thiosemicarbazide;
4-(4-carboxyphenyl)-1-[(5-hydroxy-3-methyl-1-phenylpyrazol-1-4-yl)methylene]-3-thiosemicarbazide;
4-(3-carboxyphenyl)-1-[(5-hydroxy-3-methyl-1-phenylpyrazol-4-yl)methylene]-3-thiosemicarbazide;
4-(4-carboxyphenyl)-1-[{1-(3,4-dimethylphenyl)-5-hydroxy-3-methylpyrazol-4-yl}methylene]-3-thiosemicarbazide;
4-(3-carboxyphenyl)-1-[{1-(3,4-dimethylphenyl)-5-hydroxy-3-methylpyrazol-4-yl}methylene]-3-thiosemicarbazide;
4-(4-carboxyphenyl)-1-[{5-hydroxy-3-methyl-1-(4-methylphenyl)pyrazol-4-yl}methylene]-3-thiosemicarbazide;
4-(3-carboxyphenyl)-1-[{5-hydroxy-3-methyl-1-(4-methylphenyl)pyrazol-4-yl}methylene]-3-thiosemicarbazide;
4-(carboxyphenyl)-1-[{1-(3-chlorophenyl)-5-hydroxy-3-methylpyrazol-4-yl}methylene]-3-thiosemicarbazide; and
4-(3-carboxyphenyl)-1-[{1-(3-chlorophenyl)-5-hydroxy-3-methylpyrazol-4-yl}methylene]-3-thiosemicarbazide.

Particularly preferred among the presently invented compounds are:
4-(3-carboxyphenyl)-1-[3-(3,4-dimethylphenyl)-2-hydroxybenzylidene]-3-thiosemicarbazide;
4-(4-carboxyphenyl)-1-[2-hydroxy-3-(3-trifluoromethylphenyl)benzylidene]-3-thiosemicarbazide;
4-(3-carboxyphenyl)-1-[2-hydroxy-3-(3-trifluoromethylphenyl)benzylidene-3-thiosemicarbazide;
4-(3-carboxyphenyl)-1-[3-(4-chlorophenyl)-2-hydroxybenzylidene]-3-thiosemicarbazide;
4-(4-carboxyphenyl)-1-[{5-hydroxy-3-methyl-1-(4-methylphenyl)pyrazol-4-yl}methylene]-3-thiosemicarbazide;
4-(3-carboxyphenyl)-1-[{5-hydroxy-3-methyl-1-(4-methylphenyl)pyrazol-4-yl}methylene)-3-thiosemicarbazide; and
4-(4-carboxyphenyl)-1-[{1-(3-chlorophenyl)-5-hydroxy-3-methylpyrazol-4-yl}methylene]-3-thiosemicarbazide.

Compounds of Formula (1) are included in the pharmaceutical compositions of the invention and used in the methods of the invention.

By the term "protected hydroxy" or "protected —OH" as used herein, is meant the alcoholic or carboxylic —OH groups which can be protected by conventional blocking groups in the art as described in "Protective Groups In Organic Synthesis" by Theodora W. Greene, Wiley-Interscience, 1981, New York. Compounds containing protected hydroxy groups may also be useful as intermediates in the preparation of the pharmaceutically active compounds of the invention.

By the term "aryl" as used herein, unless otherwise defined, is meant a cyclic or polycyclic aromatic ring containing from 1 to 14 carbon atoms and optionally containing from one to five heteroatoms, provided that when the number of carbon atoms is 1 the aromatic ring contains at least four heteroatoms, when the number of carbon atoms is 2 the aromatic ring contains at least three heteroatoms, when the number of carbons is 3 the aromatic ring contains at least two heteroatoms and when the number of carbon atoms is 4 the aromatic ring contains at least one heteroatom.

By the term "$C_1$–$C_{12}$aryl" as used herein, unless otherwise defined, is meant phenyl, naphthalene, 3,4-methylenedioxyphenyl, pyridine, biphenyl, quinoline, pyrimidine, quinazoline, thiophene, furan, pyrrole, pyrazole, imidazole and tetrazole.

By the term "$C_3$–$C_6$aryl" as used herein, unless otherwise defined, is meant a cyclic or polycyclic aromatic ring containing from 3 to 6 carbon atoms and optionally containing from one to 4 heteroatoms, provided that when the number of carbon atoms is 3 the aromatic ring contains at least two heteroatoms and when the number of carbon atoms is 4 the aromatic ring contains at least one heteroatom.

By the term "substituted" as used herein, unless otherwise defined, is meant that the subject chemical moiety has one or more substituents selected from the group consisting of: hydroxyalkyl, alkoxy, acyloxy, alkyl, aryl, amino, N-acylamino, hydroxy, —$(CH_2)_g$C(O)OR$^6$, —S(O)$_n$R$^7$, nitro, cyano, halogen, trifluoromethyl and protected —OH, where g is 0–6, R$^6$ is hydrogen or alkyl, n is 0–3, and R$^7$ is hydrogen or alkyl.

By the term "alkoxy" as used herein is meant —Oalkyl where alkyl is as described herein including —OCH$_3$ and —OC(CH$_3$)$_2$CH$_3$.

The term "cycloalkyl" as used herein unless otherwise defined, is meant a nonaromatic, unsaturated or saturated, cyclic or polycyclic $C_3$–$C_{12}$ Examples of cycloalkyl and substituted cycloalkyl substituents as used herein include: cyclohexyl, 4-hydroxycyclohexyl, 2-ethylcyclohexyl, propyl 4-methoxycyclohexyl, 4-methoxycyclohexyl, 4-carboxycyclohexyl and cyclopentyl.

By the term "acyloxy" as used herein is meant —OC(O)alkyl where alkyl is as described herein. Examples of acyloxy substituents as used herein include: —OC(O)CH$_3$, —OC(O)CH(CH$_3$)$_2$ and —OC(O)(CH$_2$)$_3$CH$_3$.

By the term "N-acylamino" as used herein is meant —N(H)C(O)alkyl, where alkyl is as described herein. Examples of N-acylamino substituents as used herein include: —N(H)C(O)CH$_3$, —N(H)C(O)CH(CH$_3$)$_2$ and —N(H)C(O)(CH$_2$)$_3$CH$_3$.

By the term "aryloxy" as used herein is meant —OC$_6$–C$_{12}$aryl where C$_6$–C$_{12}$aryl is phenyl, naphthyl, 3,4-methylenedioxyphenyl, pyridyl or biphenyl optionally substituted with one or more substituents selected from the group consisting of: alkyl, hydroxyalkyl, alkoxy, trifulorom-ethyl, acyloxy, amino, N-acylamino, hydroxy, —(CH$_2$)gC(O)OR$^6$, —S(O)$_n$R$^7$, nitro, cyano, halogen and protected —OH, where g is 0–6, R$^6$ is hydrogen or alkyl, n is 0–3 and R$^7$ is hydrogen or alkyl. Examples of aryloxy substituents as used herein include: phenoxy, 4-fluorophenyloxy and biphenyloxy.

By the term "heteroatom" as used herein is meant oxygen, nitrogen or sulfur.

By the term "halogen" as used herein is meant a substituent selected from bromide, iodide, chloride and fluoride.

By the term "alkyl" and derivatives thereof and in all carbon chains as used herein is meant a linear or branched, saturated or unsaturated hydrocarbon chain having $C_1$–$C_{12}$ carbon atoms. Examples of alkyl substituents as used herein include: —$CH_3$, —$CH_2$—$CH_3$, —$CH_2$—$CH_2$—$CH_3$, —$CH(CH_3)_2$, —$C(CH_3)_3$, —$(CH_2)_3$—$CH_3$, —$CH_2$—$CH(CH_3)_2$ and —$CH(CH_3)$—$CH_2$—$CH_3$, —$CH$=$CH_2$.

By the term "treating" and derivatives thereof as used herein, is meant prophylatic or therapeutic therapy.

All publications, including but not limited to patents and patent applications, cited in this specification are herein incorporated by reference as though fully set forth.

Compounds of Formula (I) are included in the pharmaceutical compositions of the invention and used in the methods of the invention. Where a —COOH or —OH group is present, pharmaceutically acceptable esters can be employed, for example methyl, ethyl, pivaloyloxymethyl, and the like for —COOH, and acetate maleate and the like for —OH, and those esters known in the art for modifying solubility or hydrolysis characteristics for use as sustained release or prodrug formulations.

The novel compounds of Formula I are prepared analogously to the processes shown in Schemes I and II below wherein wherein $R^1$, $R^2$, $R^3$, Z, Y, L and X are as defined in Formula I and provided that these substituents do not include any such substituents that render inoperative the processes of Schemes I and II. AU of the starting materials are commercially available or are readily made from commercially available starting materials by those of skill in the art.

Scheme I

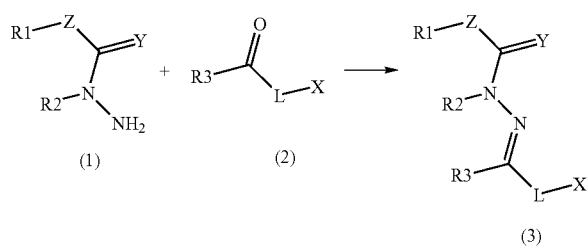

Compounds 1, are condensed with carbonyl compounds 2, available commercially or prepared by literature methods, in a suitable solvent with or without the addition of an acid catalyst such as HCl to furnish the final compound 3.

Scheme II

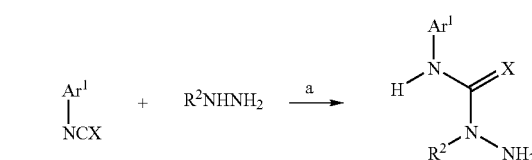

a) THF

Commercially available isocyanates or isothiocyanates are coupled with a hydrazine to produce semicarbazides or thiosemicarbazides.

The treatment of thrombocytopenia, as described herein, is accomplished by enhancing the production of platelets.

By the term "co-administering" and derivatives thereof as used herein is meant either simultaneous administration or any manner of separate sequential administration of a TPO mimetic compound, as described herein, and a further active ingredient or ingredients, known to treat thrombocytopenia, including chemotherapy-induced thrombocytopenia and bone marrow transplantation and other conditions with depressed platelet production. Preferably, if the administration is not simultaneous, the compounds are administered in a close time proximity to each other. Furthermore, it does not matter if the compounds are administered in the same dosage form, e.g. one compound may be administered topically and another compound may be administered orally.

Because the pharmaceutically active compounds of the present invention are active as TPO mimetics they exhibit therapeutic utility in treating thrombocytopenia and other conditions with depressed platelet production.

In determining potency as TPO mimetics, the following assays were employed:

*Luciferase Assay*

Compounds of the present invention were tested for potency as mimetics of the TPO receptor in a Luciferase assay such as described in Lamb, et al., *Nucleic Acids Research* 23: 3283–3289 (1995) and Seidel, et al., *Proc. Natl. Acad. Sci., USA* 92: 3041–3045 (1995) by substituting a TPO-responsive BaF3 cell line (Vigon et al. *Proc. Natl. Acad. Sci. USA* 1992, 89, 5640–5644) for the HepG2 cells utilized therein. The murine BaF3 cells express TPO receptors and closely match the pattern of STAT (signal transducers and activators of transcription) activation observed in primary murine and human bone marrow cells in response to TPO.

Some of the preferred compounds of this invention were also active in an in vitro proliferation assay using the murine 32D-mpl cell line (Bartley, T. D. et al., Cell, 1994, 77, 1117–1124). 32D-mpl cells express Tpo-R and their survival is dependent on the presence of TPO.

The pharmaceutically active compounds within the scope of this invention are useful as TPO mimetics in mammals, including humans, in need thereof.

Within the scope of the invention Compound A (found in Example 15) showed activation of about 20% of control (control is the maximal response to (TPO) at a concentration of 3 uM in the luciferase assay.

Some of the preferred compounds within the scope of the invention showed activation from about 5% to 60% control at a concentration of 0.1–30 uM in the luciferase assay. The preferred compounds of the invention also promoted the proliferation of 32D-mpl cells at a concentration of 0.01 to 30 uM.

The most preferred compounds of this invention were found to stimulate the proliferation of BAF-3/TPO-responsive human cell lines with full TPO efficacy and with $EC_{50}$ values below 100 nM as shown in Table 1.

TABLE 1

| Example # | $EC_{50}$/uM | Efficacy/%$TPO_{max}$ |
|---|---|---|
| 15.8 | 0.03 | 90 |
| 15.9 | 0.02 | 100 |

TABLE 1-continued

| Example # | EC$_{50}$/uM | Efficacy/%TPO$_{max}$ |
|---|---|---|
| 15.10 | 0.05 | 100 |
| 15.12 | 0.06 | 85 |
| 15.29 | 0.03 | 100 |
| 15.30 | 0.03 | 100 |
| 15.31 | 0.03 | 100 |

The present invention therefore provides a method of treating thrombocytopenia and other conditions with depressed platelet production, which comprises administering a compound of Formula (I), and pharmaceutically acceptable salts, hydrates, solvates and esters thereof in a quantity effective to enhance platelet production. The compounds of Formula (I) also provide for a method of treating the above indicated disease states because of their demonstrated ability to act as TPO mimetics. The drug may be administered to a patient in need thereof by any conventional route of administration, including, but not limited to, intravenous, intramuscular, oral, subcutaneous, intradermal, and parenteral.

The pharmaceutically active compounds of the present invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically active compounds in a pharmaceutical dosage unit as described above will be an efficacious, nontoxic quantity preferably selected from the range of 0.001–100 mg/kg of active compound, preferably 0.001–50 mg/kg. When treating a human patient in need of a TPO mimetic, the selected dose is administered preferably from 1–6 times daily, orally or parenterally. Preferred forms of parenteral administration include topically, rectally, transdermally, by injection and continuously by infusion. Oral dosage units for human administration preferably contain from 0.05 to 3500 mg of active compound. Oral administration, which uses lower dosages is preferred. Parenteral administration, at high dosages, however, also can be used when safe and convenient for the patient.

Optimal dosages to be administered may be readily determined by those skilled in the art, and will vary with the particular TPO mimetic in use, the strength of the preparation, the mode of administration, and the advancement of the disease condition. Additional factors depending on the particular patient being treated will result in a need to adjust dosages, including patient age, weight, diet, and time of administration.

The method of this invention of inducing TPO mimetic activity in mammals, including humans, comprises administering to a subject in need of such activity an effective TPO mimetic amount of a pharmaceutically active compound of the present invention.

The invention also provides for the use of a compound of Formula (I) in the manufacture of a medicament for use as a TPO mimetic.

The invention also provides for the use of a compound of Formula (I) in the manufacture of a medicament for use in therapy.

The invention also provides for the use of a compound of Formula (I) in the manufacture of a medicament for use in enhancing platelet production.

The invention also provides for the use of a compound of Formula (I) in the manufacture of a medicament for use in treating thrombocytopenia.

The invention also provides for a pharmaceutical composition for use as a TPO mimetic which comprises a compound of Formula (I) and a pharmaceutically acceptable carrier.

The invention also provides for a pharmaceutical composition for use in the treatment of thrombocytopenia which comprises a compound of Formula (I) and a pharmaceutically acceptable carrier.

The invention also provides for a pharmaceutical composition for use in enhancing platelet production which comprises a compound of Formula (I) and a pharmaceutically acceptable carrier.

No unacceptable toxicological effects are expected when compounds of the invention are administered in accordance with the present invention.

In addition, the pharmaceutically active compounds of the present invention can be co-administered with further active ingredients, such as other compounds known to treat thrombocytopenia, including chemotherapy-induced thrombocytopenia and bone marrow transplantation and other conditions with depressed platelet production, or compounds known to have utility when used in combination with a TPO mimetic.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXPERIMENTAL DETAILS

Example 1

4-(4-chloro-2-methylphenyl)-1-(3,5-dinitro-2-hydroxybenzylidene)-3-thiosemicarbazide The compound was obtained from a commercial source (Maybridge Chemical Company Ltd.)

Example 2

1-(3,5-dinitro-2-hydroxybenzylidene)-4-(2-methylphenyl)-3-thiosemicarbazide

The compound was obtained from a commercial source (Maybridge Chemical Company Ltd.)

Example 3

1-(3,5-dichloro-2-hydroxybenzylidene)4-(4-ethoxy-carbonylphenyl)-3-thiosemicarbazide The compound was obtained from a commercial source (Maybridge Chemical Company Ltd.)

Example 4

4-(naphth-1-yl)-1-(2,4,6-trihydroxybenzylidene)-3-thiosemicarbazide

A solution of 4-(naphth-1-yl)thiosemicarbazide (572 mg, 2.63 mmol) and 2,4,6-trihydroxybenzaldehyde (405 mg, 2.63 mmol) in acetic acid (5 mL) was heated under reflux for 20 min, then cooled. The precipitate was filtered, washed (acetic acid) and dried to give the title compound (445 mg, 54%) as a solid. MS (ES+) m/e 354 [M+H]+.

Example 5

1-(3,5-dichloro-2-hydroxybenzylidene)-4-(4-sulfophenyl)-3-thiosemicarbazide a) 4-(4-sulfophenyl)-3-thiosemicarbazide, sodium salt A solution of hydrazine in tetrahydrofuran (1M, 9.2 mL, 9.2 mmol) was added slowly to a stirred mixture of sodium 4-isothiocyanatobenzenesulfonate (2.36 g, 9.2 mmol) and tetrahydrofuran (60 mL). After 4 h, ether was added, then the solid filtered, washed (ether) and dried to give the title compound (2.47 g, 100%) as a solid. MS (ES−) m/e 246 [M−H]−.

b) 1-(3,5-dichloro-2-hydroxybenzylidene)-4-(4-sulfophenyl)-3-thiosemicarbazide

A mixture of 4-(4-sulfophenyl)-3-thiosemicarbazide, sodium salt (740 mg, 2.75 mmol), 3,5-dichloro-2-hydroxybenzaldehyde (577 mg, 3.02 mmol), concentrated aqueous hydrochloric acid (0.3 mL) and ethanol (10 mL) was heated under reflux for 20 min. then cooled. The solid was filtered, washed (water) and dried to give the title compound (277 mg, 24%) as a solid. MS (ES−) m/e 418, 420 [M−H]−.

Example 6

1-[(2-hydroxynaphth-1-yl)methylidene]-4-(4-sulfophenyl)-3-thiosemicarbazide

The procedure described in example 4 was followed here, using 4-(4-sulfophenyl)-3-thiosemicarbazide, sodium salt in place of 4-(naphth-1-yl)thiosemicarbazide and 2-hydroxy-1-naphthaldehyde in place of 2,4,6-trihydroxybenzaldehyde to give the title compound (23%) as a solid. MS (ES−) m/e 400 [M−H]−.

Example 7

4-(4-carboxyphenyl)-1-(3,5-dichloro-2-hydroxybenzylidene)-3-thiosemicarbazide

Concentrated aqueous hydrochloric acid (1 mL) was added to a stirred solution of 4-(4-carboxyphenyl)-3-thiosemicarbazide (213 mg, 1.00 mmol) and 3,5-dichloro-2-hydroxybenzaldehyde (198 mg, 1.04 mmol) in dimethylformamide (20 mL). The mixture was stirred for 18 h, water was added and the precipitate filtered, washed (water) and dried to give the title compound (212 mg, 55%) as a solid. MS (ES−) m/e 382, 384 [M−H]−.

Example 8

1-[1-(4-carboxy-2-hydroxyphenyl)ethylidene]-4-(naphth-1-yl)-3-thiosemicarbazide

The procedure described in example 7 was followed here, using 4-(naphth-1-yl)-3-thiosemicarbazide in place of 4-(4-carboxyphenyl)-3-thiosemicarbazide and 4-carboxy-2-hydroxyacetophenone in place of 3,5-dichloro-2-hydroxybenzaldehyde to give the title compound (26%) as a solid. MS (ES−) m/e 378 [M−H]−.

Example 9

4-(4-carboxyphenyl)-1-[(2-hydroxynaphth-1-yl)methylidene]-3-thiosemicarbazide

The procedure described in example 7 was followed here, using 2-hydroxy-1-naphthaldehyde in place of 3,5-dichloro-2-hydroxybenzaldehyde to give the title compound (46%) as a solid. MS (ES−) m/e 364 [M−H]−.

Example 10

4-(3-carboxyphenyl)-1-[(2-hydroxynaphth-1-yl)methylidene]-3-thiosemicarbazide

The procedure described in example 7 was followed here, using 4-(3-carboxyphenyl)-3-thiosemicarbazide in place of 4-(4-carboxyphenyl)-3-thiosemicarbazide and 2-hydroxy-1-naphthaldehyde in place of 3,5-dichloro-2-hydroxybenzaldehyde to give the title compound (49%) as a solid. MS (ES−) m/e 364 [M−H]−.

Example 11

4-(3-carboxyphenyl)-1-(3,5-dichloro-2-hydroxybenzylidene)-3-thiosemicarbazide

The procedure described in example 7 was followed here, using 4-(3-carboxyphenyl)-3-thiosemicarbazide in place of 4-(4-carboxyphenyl)-3-thiosemicarbazide to give the title compound (26%) as a solid. MS (ES−) m/e 382, 384 [M−H]−.

Example 12

1-(4-carboxy-2-hydroxybenzylidene)-4-(naphth-1-yl)-3-thiosemicarbazide

A solution of 4-(naphth-1-yl)-3-thiosemicarbazide (38 mg, 0.175 mmol) and 4 carboxy-2-hydroxybenzaldehyde (35 mg, 0.211 mmol) in dimethylformamide (2 mL) was shaken with 4 Å molecular sieves for 2.5 h. PS-TsNHNH2 resin (50 mg, 0.147 mmol) was added, shaking continued for 1 h, then the resin filtered off. Water was added to the filtrate and the precipitated solid was filtered, washed (water, ether) and dried to give the title compound (52 mg, 81%) as a solid. MS (ES+) m/e 366 [M+H]+.

Example 13

4-(4-carboxyphenyl)-1-(3,5-dibromo-2-hydroxybenzylidene)-3-thiosemicarbazide A solution of 4-(4-carboxyphenyl)-3-thiosemicarbazide (25 mg, 0.12 mmol) and 3,5-dibromo-2-hydroxybenzaldehyde (40 mg, 0.144 mmol) in dimethylsulfoxide (1 mL) was shaken with 4 Å molecular sieves for 18 h. Dimethylformamide (1 mL) was added, followed by PS-TsNHNH2 resin (80 mg, 0.230 mmol), shaking continued for 24 h, then the resin filtered off. The solution was chromatographed by reverse phase HPLC (CombiPrep ODS-A, 10–90% acetonitrile/water+0.1% trifluoroacetic acid) to give the title compound (24 mg, 42%) as a solid. MS (ES–) m/e 470, 472, 474 [M–H]–.

The following compounds were prepared by the method described in example 13:

4-(3-carboxyphenyl)-1-(3,5-dibromo-2-hydroxybenzylidene)-3-thiosemicarbazide. Yield 26%. MS (ES–) m/e 470, 472, 474 [M–H]–.

1-(4-benzyloxy-2-hydroxybenzylidene)-4-(4-carboxyphenyl)-3-thiosemicarbazide. Yield 35%. MS (ES–) m/e 420 [M–H]–.

1-(1-benzyloxy-2-hydroxybenzylidene)-4-(3-carboxyphenyl)-3-thiosemicarbazide. Yield 16%. MS (ES–) m/e 420 [M–H]–.

4-(3-carboxyphenyl)-1-(5-chloro-2-hydroxybenzylidene)-3-thiosemicarbazide. Yield 33%. MS (ES–) m/e 348, 350 [M–H]–.

4-(4-carboxyphenyl)-1-[(1-hydroxynaphth-2-yl)methylidene]-3-thiosemicarbazide. Yield 50%. MS (ES–) m/e 364 [M–H]–.

4-(3-carboxyphenyl)-1-[(1-hydroxynaphth-2-yl)methylidene]-3-thiosemicarbazide. Yield 41%. MS (ES–) m/e 364 [M–H]–.

4-(4-carboxyphenyl)-1-(3,5-di-t-butyl-2-hydroxybenzylidene)-3-thiosemicarbazide. Yield 37%. MS (ES–) m/e 426 [M–H]–.

4-(3-carboxyphenyl)-1-(3,5-di-t-butyl-2-hydroxybenzylidene)-3-thiosemicarbazide. Yield 22%. MS (ES–) m/e 426 [M–H]–.

4-(4-carboxyphenyl)-1-(2-hydroxy-3-methylbenzylidene)-3-thiosemicarbazide. Yield 18%. MS (ES–) m/e 328 [M–H]–.

4-(3-carboxyphenyl)-1-(2-hydroxy-3-methylbenzylidene)-3-thiosemicarbazide. Yield 15%. MS (ES–) m/e 328 [M–H]–.

4-(3-carboxyphenyl)-1-(2-hydroxy-5-methylbenzylidene)-3-thiosemicarbazide. Yield 40%. MS (ES–) m/e 328 [M–H]–.

Example 14

1-(2,4-dihydroxybenzylidene)-4-(naphth-1-yl)-3-thiosemicarbazide

A solution of 4-(naphth-1-yl)-3-thiosemicarbazide (26 mg, 0.12 mmol) and 2,4-dihydroxybenzaldehyde (20 mg, 0.144 mmol) in dimethylformamide (1 mL) was shaken with 4 Å molecular sieves for 60 h. PS-TsNHNH2 resin (29 mg, 0.085 mmol) was added and shaking continued for 40 h, then the resin was filtered off. The solvent was removed under vacuum and the residue dissolved in ethanol. The solvent was again removed and the process repeated to give the title compound (7 mg, 18%) as a solid. MS (ES–) m/e 336 [M–H]–.

The following compounds were prepared by the method described in example 14:

1-(2-hydroxy-3-carboxybenzylidene)-4-(2-phenylphenyl)-3-thiosemicarbazide. Yield 14%. MS (ES–) m/e 390 [M–H]–.

4-(3-chloro-2-methylphenyl)-1-(2-hydroxy-4-carboxybenzylidene)-3-thiosemicarbazide. Yield 21%. MS (ES–) m/e 362, 364 [M–H]–.

1-(2-hydroxy-4-carboxybenzylidene)-4-(2-phenylphenyl)-3-thiosemicarbazide. Yield 11%. MS (ES–) m/e 390 [M–H]–.

4-(3-chloro-4-methylphenyl)-1-(2-hydroxy-4-carboxybenzylidene)-3-thiosemicarbazide. Yield 14%. MS (ES–) m/e 362, 364 [M–H]–.

1-(2-hydroxy-4-carboxybenzylidene)-4-(4-methylphenyl)-3-thiosemicarbazide. Yield 15%. MS (ES–) m/e 328 [M–H]–.

Example 15

4-(4-carboxyphenyl)-1-[2-methoxy-3-(4-methylphenyl)benzylidene]-3-thiosemicarbazide.

A solution of 4-(4-carboxyphenyl)-3-thiosemicarbazide (11 mg, 0.05 mmol) and 2-methoxy-3-(4-methylphenyl)benzaldehyde (14 mg, 0.06 mmol) in dimethylformamide (1 mL) was shaken with 4 Å molecular sieves for 40 h. PS-TsNHNH2 resin (17 mg, 0.05 mmol) was added and shaking continued for 24 h, then the resin was filtered off. The solvent was removed under vacuum and the residue chromatographed by reverse phase HPLC (CombiPrep ODS-A, 10–90% acetonitrile/water+0.1% trifluoroacetic acid) to give the title compound (3 mg, 14%) as a solid. MS (ES–) m/e 418 [M–H]–.

The following compounds were prepared by the method described in example 15:

4-(3-carboxyphenyl)-1-[3-(4-fluorophenyl)-2-methoxybenzylidene]-3-thiosemicarbazide. Yield 36%. MS (ES–) m/e 422 [M–H]–.

4-(4-carboxyphenyl)-1-[3-(4-chlorophenyl)-2-methoxybenzylidene]-3-thiosemicarbazide. Yield 32%. MS (ES–) m/e 438, 440 [M–H]–.

4-(3-carboxyphenyl)-1-[3-(4-chlorophenyl)-2-methoxybenzylidene]-3-thiosemicarbazide. Yield 50%. MS (ES–) m/e 438, 440 [M–H]–.

4-(4-carboxyphenyl)-1-[3-(dibenzo[b,d]furan-1-yl)-2-methoxybenzylidene]-3-thiosemicarbazide. Yield 36%. MS (ES–) m/e 494 [M–H]–.

4-(4-carboxyphenyl)-1-[2-hydroxy-3-(2-methylphenyl)benzyhdene]-3-thiosemicarbazide. Yield 35%. MS (ES–) m/e 404 [M–H]–.

4-(3-carboxyphenyl)-1-[2-hydroxy-3-(2-methylphenyl)benzylidene]-3-thiosemicarbazide. Yield 24%. MS (ES–) m/e 404 [M–H]–.

4-(4-carboxyphenyl)-1-[3-(3,4-dimethylphenyl)-2-hydroxybenzylidene]-3-thiosemicarbazide. Yield 25%. MS (ES–) n/e 418 [M–H]–.

4-(3-carboxyphenyl)-1-[3-(3,4-dimethylphenyl)-2-hydroxybenzylidene]-3-thiosemicarbazide. Yield 33%. MS (ES–) m/e 418 [M–H]–. (Ex.# 15.8-Compound A)

4-(4-carboxyphenyl)-1-[2-hydroxy-3-(3-trifluoromethylphenyl)benzylidene]-3-thiosemicarbazide. Yield 27%. MS (ES–) m/e 458 [M–H]–. (Ex # 15.9 -Compound B)

4-(3-carboxyphenyl)-1-[2-hydroxy-3-(3-trifluoromethylphenyl)benzylidene]-3-3-thiosemicarbazide. Yield 41%. MS (ES−) m/e 458 [M−H]−. (Ex.# 15.10-Compound C)

4-(4-carboxyphenyl)-1-[3-(4-fluorophenyl)-2-hydroxybenzylidene]-3-thiosemicarbazide. Yield 33%. MS (ES−) m/e 408 [M−H]−.

4-(3-carboxyphenyl)-1-[3-(4-chlorophenyl)-2-hydroxybenzylidene]-3-thiosemicarbazide. Yield 26%. MS (ES−) m/e 424 [M−H]−. (Ex. # 15.12-Compound D)

4-(4-carboxyphenyl)-1-[3-(dibenzo[b,d]furan-1-yl)-2-hydroxybenzylidene]-3-thiosemicarbazide. Yield 42%. MS (ES−) m/e 480 [M−H]−.

4-(3-carboxyphenyl)-1-[3-(dibenzo[b,d]furan-1-yl)-2-hydroxybenzylidene]-3-thiosemicarbazide. Yield 50%. MS (ES−) m/e 480 [M−H]−.

4-(4-carboxyphenyl)-1-[2-hydroxy-3-(naphth-1-yl)benzylidene]-3-thiosemicarbazide. Yield 21%. MS (ES−) m/e 440 [M−H]−.

4-(3-carboxyphenyl)-1-[2-hydroxy-3-(naphth-1-yl)benzylidene]-3-thiosemicarbazide. Yield 33%. MS (ES−) m/e 440 [M−H]−.

4-(4-carboxyphenyl)-1-[3-(3-chlorophenyl)-2-hydroxybenzylidene]-3-thiosemicarbazide. Yield 25%. MS (ES−) m/e 424, 426 [M−H]−.

4-(3-carboxyphenyl)-1-[3-(3-chlorophenyl)-2-hydroxybenzylidene]-3-thiosemicarbazide. Yield 40%. MS (ES−) m/e 424, 426 [M−H]−.

4-(4-carboxyphenyl)-1-[2-hydroxy-3-(3-nitrophenyl)benzylidene]-3-thiosemicarbazide. Yield 30%. MS (ES−) m/e 435 [M−H]−.

4-(3-carboxyphenyl)-1-[2-hydroxy-3-(3-nitrophenyl)benzylidene]-3-thiosemicarbazide. Yield 35%. MS (ES−) m/e 435 [M−H]−.

4-(4-carboxyphenyl)-1-(2-hydroxy-4-phenylbenzylidene)-3-thiosemicarbazide. Yield 28%. MS (ES−) m/e 390 [M−H]−.

4-(3-carboxyphenyl)-1-(2-hydroxy-4-phenylbenzylidene)-3-thiosemicarbazide. Yield 49%. MS (ES−) m/e 390 [M−H]−.

4-(4-carboxyphenyl)-1-[{1-(4-chlorophenyl)-5-hydroxy-3-methylpyrazolyl}methylene]-3-thiosemicarbazide. Yield 39%. MS (ES−) m/e 428, 430H]−.

4-(3-carboxyphenyl)-1-[{1-(4-chlorophenyl)-5-hydroxy-3-methylpyrazol]-4-yl}methylene]-3-thiosemicarbazide. Yield 27%. MS (ES−) m/e 428, 430 [M−H]−.

4-(4-carboxyphenyl)-1-[{(5-hydroxy-3-methyl-1-phenylpyrazol-4-yl}methylene]-3-thiosemicarbazide. Yield 40%. MS (ES−) m/e 394 [M−H]−.

4-(3-carboxyphenyl)-1-[(5-hydroxy-3-methyl-1-phenylpyrazol-4-yl)methylene]-3-thiosemicarbazide. Yield 49%. MS (ES−) m/e 394 [H]−.

4-(4-carboxyphenyl)-1-[{1-(3,4-dimethylphenyl)-5-hydroxy-3-methylpyrazol]-4-yl}methylene]-3-thiosemicarbazide. Yield 35%. MS (ES−) m/e 422 [M−H]−.

4-(3-carboxyphenyl)-1-[{1-(3,4-dimethylphenyl)-5-hydroxy-3-methylpyrazol-4-yl}methylene]-3-thiosemicarbazide. Yield 39%. MS (ES−) m/e 422 [M−H]−.

4-(4-carboxyphenyl)-1-[{5-hydroxy-3-methyl-1-(4-methylphenyl)pyrazol-4-yl}methylene]-3-thiosemicarbazide. Yield 31%. MS (ES−) m/e 408 [M−H]−. (Ex.# 15.29-Compound E)

4-(3-carboxyphenyl)-1-[{5-hydroxy-3-methyl-1-(4-methylphenyl)pyrazol-4-yl}methylene]-3-thiosemicarbazide. Yield 41%. MS (ES−) m/e 408 [M−H]−. (Ex.# 15.30-Compound F)

4-(4-carboxyphenyl)-1-[{1-(3-chlorophenyl)-5-hydroxy-3-methylpyrazol-4-yl}methylene]-3-thiosemicarbazide. Yield 29%. MS (ES−) m/e 428, 430 [M−H]−.(Ex.# 15.31-Compound G)

4-(3-carboxyphenyl)-1-[{1-(3-chlorophenyl)-5-hydroxy-3-methylpyrazol-4-yl}methylene]-3-thiosemicarbazide. Yield 21%. MS (ES−) m/e 428, 430 [M-1H]−.

Example 16

Capsule Composition

An oral dosage form for administering a presently invented agonist of the TPO receptor is produced by filing a standard two piece bard gelatin capsule with the ingredients in the proportions shown in Table II, below.

TABLE II

| INGREDIENTS | AMOUNTS |
|---|---|
| 4-(3-carboxyphenyl)-1-[3-(3,4-dimethylphenyl)-2-hydroxybenzylidene]-3-thiosemicarbazide (Compound A) | 20 mg |
| Lactose | 55 mg |
| Talc | 16 mg |
| Magnesium Stearate | 4 mg |

Example 17

Injectable Parenteral Composition

An injectable form for administering a presently invented agonist of the TPO receptor is produced by stirring 1.5% by weight of 4-(3-carboxyphenyl)-1-[3-(3,4 dimethylphenyl)-2-hydroxybenzylidene]-3-thiosemicarbazide (Compound A), in 10% by volume propylene glycol in water.

Example 18

Tablet Composition

The sucrose, calcium sulfate dihydrate and a presently invented agonist of the TPO receptor, as shown in Table III below, are mixed and granulated in the proportions shown with a 10% gelatin solution. The wet granules are screened, dried, mixed with the starch, talc and stearic acid, screened and compressed into a tablet.

TABLE III

| INGREDIENTS | AMOUNTS |
|---|---|
| 4-(3-caxboxyphenyl)-1-[3-(3,4-dimethylphenyl)-2-hydroxybenzylidene]-3-thiosemicarbazide (Compound A) | 20 mg |
| calcium sulfate dihydrate | 30 mg |
| sucrose | 4 mg |
| starch | 2 mg |
| talc | 1 mg |
| stearic acid | 0.5 mg |

Particularly preferred among the compounds of the present invention are the following.

4-(4-carboxyphenyl)-1-[3-(3,4-dimethylphenyl)-2-hydroxybenzylidene]-3-thiosemicarbazide;

4-(3-carboxyphenyl)-1-[3-(3,4-dimethylphenyl)-2-hydroxybenzylidene]-3-thiosemicarbazide;

4-(4-carboxyphenyl)-1-[2-hydroxy-3-(3-trifluoromethylphenyl)benzylidene]-3-thiosemicarbazide;

4-(3-carboxyphenyl)-1-[2-hydroxy-3-(3-trifluoromethylphenyl)benzylidene]-3-thiosemicarbazide;

4-(4-carboxyphenyl)-1-[3-(4-fluorophenyl)-2-hydroxybenzylidene]-3-thiosemicarbazide;

4-(3-carboxyphenyl)-1-[3-(4-chlorophenyl)-2-hydroxybenzylidene]-3-thiosemicarbazide;

4-(4-carboxyphenyl)-1-[3-(dibenzo [b,d]furan-1-yl)-2-hydroxybenzylidene]-3-thiosemicarbazide;

4-(4-carboxyphenyl)-1-[2-hydroxy-3-(naphth-1-yl)benzylidene]-3-thiosemicarbazide;

4-(3-carboxyphenyl)-1-[2-hydroxy-3-(naphth-1-yl)benzylidene]-3-thiosemicarbazide;

4-(4-carboxyphenyl)-1-[3-(3-chlorophenyl)-2-hydroxybenzylidene]-3-thiosemicarbazide;

4-(3-carboxyphenyl)-1-[3-(3-chlorophenyl)-2-hydroxybenzylidene]-3-thiosemicarbazide;

4-(4-carboxyphenyl)-1-[{1-(3,4-dimethylphenyl)-5-hydroxy-3-methylpyrazol-4-yl}methylene]-3-thiosemicarbazide;

4-(3-carboxyphenyl)-1-[{1-(3,5-dimethylphenyl)-5-hydroxy-3-methylpyrazol-4-yl}methylene]-3-thiosemicarbazide;

4-(4-carboxyphenyl)-1-[{5-hydroxy-3-methyl-1-(4-methylphenyl)pyrazol-4-yl}methylene]-3-thiosemicarbazide;

4-(3-carboxyphenyl)-1-[{5-hydroxy-3-methyl-1-(4-methylphenyl)pyrazol-4-yl}methylene]-3-thiosemicarbazide; and 4-(4-carboxyphenyl)-1-[{1-(3-chlorophenyl)-5-hydroxy-3-methylpyrazol-4-yl}methylene]-3-thiosemicarbazide.

While the preferred embodiments of the invention are illustrated by the above, it is to be understood that the invention is not limited to the precise instructions herein disclosed and that the right to all modifications coming within the scope of the following claims is reserved.

What is claimed is:

1. A compound selected from:

4-(naphth-1-yl)-1-(2,4,6-trihydroxybenzylidene)-3-thiosemicarbazide;

1-[(2-hydroxynaphth-1-yl)methylidene]-4-(4-sulfophenyl)-3-thiosemicarbazide;

1-[1-(4-carboxy-2-hydroxyphenyl)ethylidene]-4-(naphth-1-yl)-3-thiosemicarbazide;

4-(4-carboxyphenyl)-1-[(2-hydroxynaphth-1-yl)methylidene]-3-thiosemicarbazide;

4-(3-carboxyphenyl)-1-[(2-hydroxynaphth-1-yl)methylidene]-3-thiosemicarbazide;

1-(4-carboxy-2-hydroxybenzylidene)-4-(naphth-1-yl)-3-thiosemicarbazide;

4-(4-carboxyphenyl)-1-[(1-hydroxynaphth-2-yl)methylidene]-3-thiosemicarbazide;

4-(3-carboxyphenyl)-1-[(1-hydroxynaphth-2-yl)methylidene]-3-thiosemicarbazide;

1-(2,4-dihydroxybenzylidene)-4-(naphth-1-yl)-3-thiosemicarbazide;

4-(4-carboxyphenyl)-1-[2-hydroxy-3-(naphth-1-yl)benzylidene]-3-thiosemicarbazide; and 4-(3-carboxyphenyl)-1-[2-hydroxy-3-(naphth-1-yl)benzylidene]-3-thiosemicarbazide.

* * * * *